United States Patent [19]

L'Esperance, Jr.

[11] Patent Number: 5,257,988
[45] Date of Patent: Nov. 2, 1993

[54] APPARATUS FOR PHACOEMULSIFYING CATARACTOUS-LENS TISSUE WITHIN A PROTECTED ENVIRONMENT

[75] Inventor: Francis A. L'Esperance, Jr., Englewood, N.J.

[73] Assignee: L'Esperance Medical Technologies, Inc., New York, N.Y.

[21] Appl. No.: 732,801

[22] Filed: Jul. 19, 1991

[51] Int. Cl.[5] .......................................... A61B 17/36
[52] U.S. Cl. ................................. 606/6; 606/4; 606/12; 606/15; 604/21; 604/22; 607/89
[58] Field of Search .................. 606/2, 4, 6, 7, 12–16; 604/20, 21, 22; 128/395, 786

[56] References Cited

U.S. PATENT DOCUMENTS

| | | | |
|---|---|---|---|
| 3,732,858 | 5/1973 | Banko | 604/22 |
| 4,246,902 | 1/1981 | Martinez | 604/22 |
| 4,589,414 | 5/1986 | Yoshida et al. | 604/22 |
| 4,760,840 | 8/1988 | Fournier, Jr. et al. | 606/16 |
| 4,825,865 | 5/1989 | Zelman | 606/107 |
| 4,963,142 | 10/1990 | Loertscher | 606/14 |
| 4,985,027 | 1/1991 | Dressel | 606/15 |
| 4,993,412 | 2/1991 | Murphy-Chutorian | 606/7 |
| 5,061,266 | 10/1991 | Hakky | 606/15 |
| 5,106,364 | 4/1992 | Hayafuji et al. | 604/22 |
| 5,112,299 | 5/1992 | Pascaloff | 604/22 |
| 5,123,902 | 6/1992 | Müller et al. | 606/4 |
| 5,129,896 | 7/1992 | Hasson | 606/16 |
| 5,176,628 | 1/1993 | Charles et al. | 604/22 |

*Primary Examiner*—Stephen C. Pellegrino
*Assistant Examiner*—Jeffrey A. Schmidt
*Attorney, Agent, or Firm*—Hopgood, Calimafde, Kalil, Blaustein & Judlowe

[57] ABSTRACT

An instrument for ophthalmic surgery to remove cataractous-lens tissue has an elongate stem which enables external manipulation at its proximal end and which at its distal end presents a cutter adjacent a transiently open cavity into which cut or chopped tissue can be manipulated. The instrument provides for selectively operated closure of the thus-loaded cavity, an event which must occur before laser radiation can issue within the cavity, in fragmenting or emulsifying reduction of cut or chopped tissue within the cavity. Thus, reduced, the fragmented material is extracted by an aspirating flow of liquid. This process is repeated until the capsulary bag has been cleared of cataractous material, be it nuclear or cortical.

28 Claims, 2 Drawing Sheets

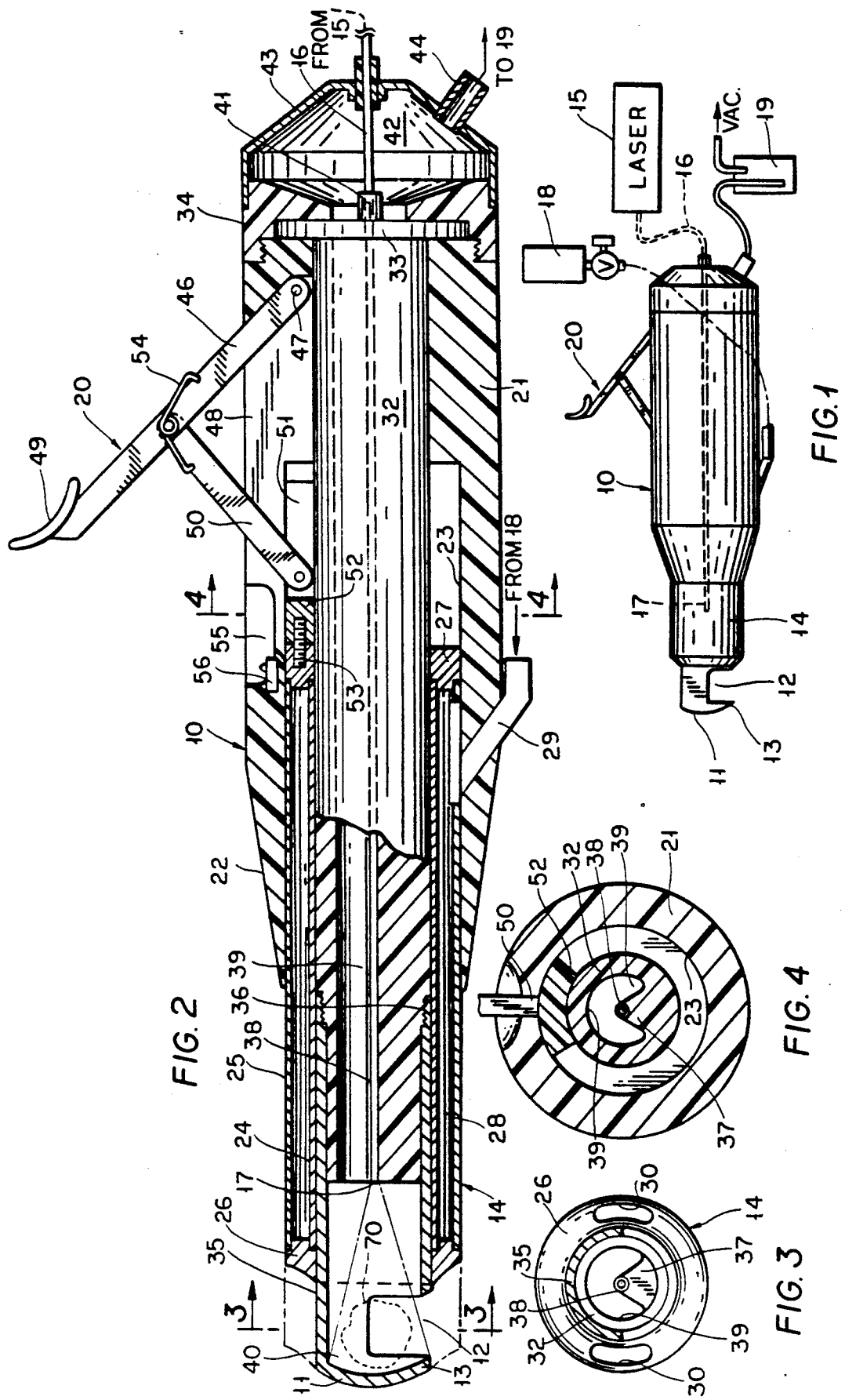

APPARATUS FOR PHACOEMULSIFYING CATARACTOUS-LENS TISSUE WITHIN A PROTECTED ENVIRONMENT

BACKGROUND OF THE INVENTION

The present invention relates to surgically invasive apparatus for accessing a cataracted natural lens via the anterior chamber and a dilated iris, and for removing cataractous material from the lens.

Within the last ten years, there have been important advances in instrumentation and techniques for removal of cataractous-lens material. What has been termed phacoemulsification is perhaps the most important of these advances, and it should be noted that this term has applied to the use of ultrasonic energy, delivered at the small tip of a piezoelectric or magnetostrictive device; this is the currently favored means of locally fragmenting cataractous tissue, for extraction via a continuous flow of benign liquid. But use of such phacoemulsification devices calls for great skill, in that excessive delivery or misdirected delivery of ultrasonic energy can result in irreparable damage to the capsulary bag, the corneal endothelium, the retina and/or other parts of the eye.

It has also been proposed, but not generally accepted, to use local delivery of laser radiation to fragment cataractous material, to an extent permitting extraction in a continuous flow of irrigating liquid. But again, there is the prospect of irreversible damage to other parts of the eye, and great surgical skill is required.

Recent announcements have described another potential improvement in cataract surgery, attributed to Dr. J. M. Dodick, who uses the expression "laser phacolysis" in describing his procedure.* The Dodick procedure uses a 1,064-nm Nd:YAG laser to supply energy via an optical fiber. The energy is delivered within the probe tip of his instrument, for reflection by a titanium target that is inclined within the otherwise open end of the probe tip. Resulting shock waves are said to cause the nucleus and cortex to be lysed, and the debris is then aspirated out of the eye.

*"Use of Neodymium-YAG Laser for Removal of Cataracts is Reported", *Ophthalmology Times*, Dec. 15, 1989, pages 1, 6; "Nontarget Tissue of Rabbit Eyes Unharmed by Nd:YAG Phacolysis", *Ophthalmology Times*, Apr. 15, 1990, pages 1, 31; "Will Laser Become the Cataract Surgery Instrument of the '90s?", *Ophthalmology Times*, Aug. 1, 1990, page 40.

Throughout this case, the terms phacoemsulsification, phacolysis and tissue-fragmentation are deemed to be synonymous, in the sense that they apply to the use of externally supplied and locally delivered energy, whether ultrasonically applied or laser radiated, to break up and reduce cataractous material to a particular size small enough for external removal by the flow of an irrigating liquid.

BRIEF STATEMENT OF THE INVENTION

It is an object of the invention to provide an improved apparatus and technique for removal of cataractous-lens tissue.

A specific object is to achieve the foregoing object by means whereby tissue-fragmentation or emulsification can proceed in an instrument-protected environment, such that the energy delivered for fragmentation or emulsification cannot damage other parts of an eye.

Another specific object is to achieve the above objects with an instrument which embodies its own means of infusing and extracting a flow of liquid at the situs of fragmentation.

Still another object is to provide in apparatus of the character indicated a safety feature whereby no laser energy can be radiated within the eye unless the cataractous tissue to be fragmented is in an instrument-protected environment.

The invention achieves these objects in an instrument having an elongate stem which enables external manipulation at its proximal end and which at its distal end presents a cutter adjacent a transiently open cavity into which cut or chopped tissue can be manipulated. The instrument provides for selectively operated closure of the thus-loaded cavity, an event which must occur before laser radiation can issue within the cavity, in fragmenting or emulsifying reduction of cut or chopped tissue within the cavity. Thus, reduced, the fragmented material is extracted by an aspirating flow of liquid. This process is repeated until the capsulary bag has been cleared of cataractous material, be it nuclear or cortical.

DETAILED DESCRIPTION

Preferred and other embodiments of the invention will be described in detail, in conjunction with the accompanying drawings. In said drawings;

FIG. 1 is a simplified overall view of a phacoemulsifying instrument of the invention, together with external devices involved in operation of the instrument;

FIG. 2 is an enlarged longitudinal sectional view of the instrument of FIG. 1;

FIG. 3 is a sectional view, taken at 3—3 in FIG. 2;

FIG. 4 is another sectional view, taken at 4—4 in FIG. 2;

Figure 5:
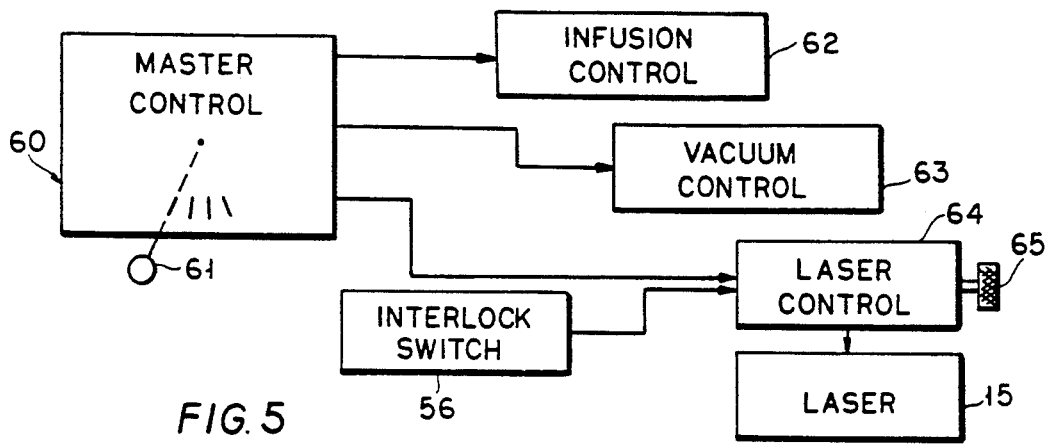
FIG. 5 is a simplified block diagram of a control system for the instrument of FIG. 2.
Figure 6:
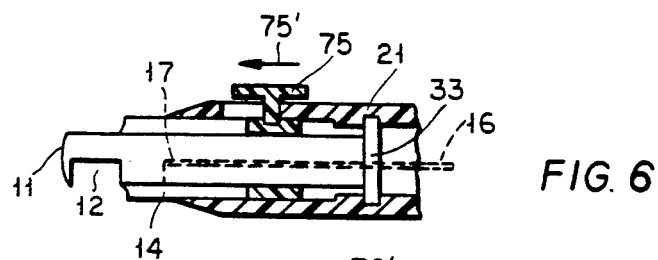
FIG. 6 is a highly schematic diagram to illustrate a basic function of the instrument of FIG. 2.

The system of FIG. 1 is seen to comprise a hand-held instrument 10 that is centrally open to a wall 11 at its distal end. Wall 11 is adjacent a side port 12, thereby defining a laterally projecting free cutter 13 whereby cataractous tissue may be excavated and scooped through the side port and into the centrally open or chamber region of the distal end. The side port 12 is open or closed by selective manipulation of a sleeve member 14 which, in the preferred embodiment, can be longitudinally shifted between its retracted position (as shown), to its forward position of total side-port closure, thus totally enclosing the scooped lens material within the chamber region of the distal end. Laser radiation from an external source 15 is deliverable via an optical-fiber cable 16 that is guided within the instrument for laser discharge at 17, directed at scooped material in the closed chamber region of the distal end of the instrument. Provision is made for a controlled flow of infusion liquid from a source 18 to a first elongate cannula within the instrument, for ported external discharge near the distal end, and a second elongate cannula within the instrument communicates between the distal chamber region and an external evacuation system including a trap 19 for aspiration and collection of fragmented lens material. A lever system 20 is shown for actuated forward displacement of sleeve 14 into port (12) closing position.

Referring now to FIGS. 2 to 4, the instrument 10 will be seen to be contained and manipulated via an elongate tubular handle member 21, which will be understood in FIG. 2 to have been longitudinally foreshortened for better showing of detail. The distal end of handle member 21 is characterized by a gently reducing external surface 22 and by a cylindrical bore 23 for longitudinal guidance of the port-closing sleeve 14.

Sleeve 14 is shown to comprise inner and outer tubular members 24, 25 which are concentrically spaced by distal and proximal end fitments 26, 27, to thereby define a first or outer annular cannula 28 which receives a flow of infusion liquid, such as a balanced saline solution, via an inlet-port connection 29 from source 18, and which discharges this flow via end ports 30 (FIG. 3) in the distal fitment 26. The concave sectional profile of the distal end fitment 26 will be understood to suggest a sharp circular cutting edge of fitment 26, adjacent the cylindrical outer surface of the inner cannula on which it is slidably guided.

The distal end-closure wall 11 is a part of a second or inner cannula assembly having a cylindrical outer surface for further stabilizing guidance of the displaceable sleeve. As shown, this assembly comprises an elongate proximal member 32 having a radial flange formation 33 whereby member 33 may be fixedly retained by and between clamp formations of a nut fitment 34 that is removably threaded to the proximal end of handle 21. The distal end wall 11 and its side port 12 are distal formations of an otherwise tubular end member 35 having removably threaded engagement at 36 to the distal end of member 32. A local sector formation 37 (FIG. 4) in the otherwise open bore 39 of member 32 extends longitudinally for central rigid positioning of a piloting tube 38 for guided retention of the optical-fiber cable 16. As previously explained, the distal end of the optical fiber is poised for discharge at 17, which is seen in FIG. 2 to be the distal end of member 32 and which is also seen to be at sufficient longitudinal offset from end wall 11 to permit divergent laser discharge from the optical-fiber end to cover the entire sectional area of the containment chamber 40 defined upon closure of side port 12. The optical-fiber cable 16 is protected at proximal-end entry into its guide tube 38, by a resilient bushing 41, as of silicone rubber, carried locally by member 32 and having light frictional retaining engagement to cable 16, whereby to retain fiber discharge at 17.

The open bore 39 of member 32 establishes the inner cannula which communicates from the distal fragmentation chamber 40 to a proximal chamber 42 defined by an end-bell portion 43 which, with nut formation 34, is a detachable subassembly to handle 21. The end-bell portion 43 is shown with a port fitment 44, adapted for slip-fitted flexible connection to the aspiration device 19.

Various means may be devised for selective or automated actuation of sleeve 14 between its displacement limits of side-port (12) opening and closure. The lever system 20 that is shown is somewhat schematic, involving a primary lever 46 which has pivoted reference at 47 to handle 21 via an elongate slot, one wall 48 of which is depicted in FIG. 2. Lever 46 projects outwardly when sleeve 14 is retracted, exposing its finger-pad formation 49 in readiness for squeezed displacement between slot walls 48. A link 50 connects lever 46 to the slotted end 51 of a cylindrically arcuate slide block 52, and a close-threaded element 53 connects block 52 to the proximal-end closure fitment of slide 14. A spring 54 at connection of link 50 to lever 46 is preloaded to normally draw lever 46 to its outward position, thus normally returning slide 14 to its retracted position. When lever 46 has been fully squeezed into slot 48, with finger pad 46 contained within a local recess 55, an electrical interlock switch 56 will have been actuated, to certify that slide 14 has fully closed port 12 to chamber 40. Switch 56 will be understood to provide a safety function, precluding laser discharge into the optical-fiber delivery cable 16, unless and until port 12 is thus certified to have been fully closed.

Operation and use of the instrument and system of FIGS. 1 to 4 will be illustratively described in further connection with control components schematically shown in FIG. 5, wherein a foot-operated master control unit 60 includes a multiple-position control lever 61, for determining selectively available sequencing operations of an infusion-flow control 62 for liquid from source 18, a vacuum-flow control 63 for control of aspirating flow into the collection device 19, and on-off control means 64 for the release of laser (15) radiation into the optical-fiber cable 16. Control means 64 is schematically shown with manual-adjustment means 65, whereby selection can be made of the duration of any given laser radiation within chamber 40; for example, for a pulsed-laser delivery, adjustment at 65 may preset the desired number and strength of pulsed-laser delivery to chamber 40, for a given exposure release. Finally, the interlock switch 56 is shown with connection to the laser-control means 64 whereby, regardless of the foot-operated positioning of the master-control element 61, there can be no laser discharge into chamber 40, unless chamber 40 is certified (by switch 56) to have been fully closed at port 12.

In assembling the described instrument prior to cataract extraction, the autoclavable or otherwise aseptic portion (e.g., the disposable distal end member 35) is first assembled to the more proximal member 32, thereby assuring that the distal cataract-grasping portion for each patient operation will be new and sharp (at 13) for every cataract extraction. Next, the fiber optic cable 16, which is preferably steel-clad, flexible and sterile, is threaded, first loosely through silicone bushing in end bell 43 and then through bushing 41 and the central guide tube 38 until the fiber end at 17 is flush with the distal end of the inner cannula member 32. At the proximal end of accommodation by member 32, the fiber optic cable 16 is frictionally held in place by the silicone bushing 41, which minimizes destructive movement of cable 16. The entire inner cannula assembly is then inserted within handle 21 and the bore of sleeve 14, to the point of flange 33 abutment with the proximal end of handle 21; this position is retained by removable assembly of nut 34 to handle 21. The inner cannula has then become fixed to the handle, with the wall 11, side port 12 and chamber 40 located forward of the retracted distal end of sleeve 16. And the ports to infusion and aspiration parts of the instrument can be connected to devices 18, 19, while the fiber optic cable is detachably coupled to laser 15.

In operation, the instrument is first manipulated to remove cortex tissue from the anterior surface of a cataracted lens, and it is further manipulated to engage and pass through port 12 a relatively large chunk 70 of cataractous nuclear tissue. Lever 46 is then depressed to close the side port 12 and in the process to sever the chunk of cataract tissue which passed through port 12 and which is therefore positioned in chamber 40, in readiness for laser irradiation from the locally contained source 17. The fully isolated and contained chunk 70 of cataract tissue can then be fragmented or emulsified by a delivered burst of 3 to 30 pulses of a neodymium-YAG or other laser, involving pulse energies ranging from 1 to 40 millijoules, illustratively with pulse durations of 150 to 300 microseconds. The emulsified or fragmented cataractous material is then vacuum-aspirated with a scavenging liquid flow, back through passage 39 in the inner cannula 32 to aspiration port 44 and then to the external drip container or trap 19. Illustratively, aspiration of the described system is controlled by a commercially available, selectively variable aspiration device, set to create a vacuum condition in the range 100 to 500-mm Hg.

Concurrently with the aspiration procedure, balanced saline or other solution is allowed to enter the instrument and to discharge at 30, to refill or replace the portion of the cataract that has been aspirated. The balanced saline solution contained at 18 would be located approximately 65-cm above the level of eye surgery, but it will be understood that this particular level should be adjustable in the range 10 to 65-cm, as required to maintain appropriate intralenticular or intraocular pressure.

When the entire nuclear portion of the cataract has been removed, by one or more cycles of the described procedure, having been emulsified or fragmented by the laser energy, the procedure of irrigation (infusion) via ports 30 and aspiration of the cortex of the cataract can be performed in customary manner. For this purpose, one of the settings of the master control 60 will be understood to determine solely the concurrent flows of infusion and aspiration, with side port 12 open (i.e., sleeve 14 retracted). Such concurrent flows can continue until all cortical material has been stripped from the inner wall of the capsulary bag, thus leaving the lens capsule free of cortical and nuclear material.

In describing various embodiments of the invention in connection with FIGS. 6 to 9, it is convenient to adopt a schematic technique, from which individual differences between embodiments can be readily identified. In all of these cases, it will be understood that provision for infusion and aspiration flows can be substantially as described for FIGS. 1 to 4. For purposes of comparison, the first of these schematic showings (FIG. 6) will be recognized as illustrating the preferred embodiment of FIGS. 1 to 4, wherein a longitudinally slidable actuating button 75 replaces the lever system 20 as the means of selective longitudinal displacement of sleeve 14, to control opening and closure of side port 12, it being noted that end wall 11, its adjacent side port 12 and chamber region 40 are all fixedly related to handle 21. The directional arrow 75' indicates the direction of button 75 actuation, to drive sleeve 14 from the open to the closed condition of side port 12.

Figure 7:
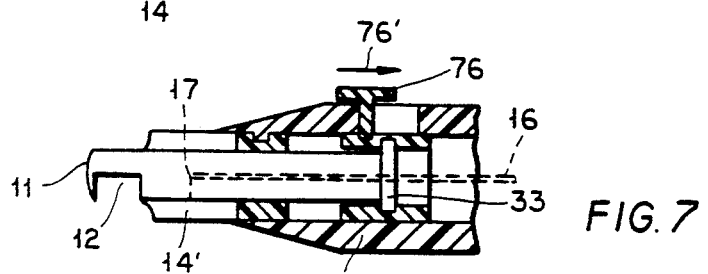
FIG. 7 is a diagram similar to FIG. 6, to show a first modification.

The arrangement of FIG. 7 will accomplish the purposes of FIGS. 1 to 4 and 6, but in FIG. 7, a longitudinally slidable actuating button 76 is displaced in the opposite direction (arrow 76') to effect side port (12) closure by a rearward retraction of the inner cannula, via button 76 engagement to the flange 33. In this arrangement, the outer-sleeve cannula 14' is fixed to handle 21.

Figure 8:
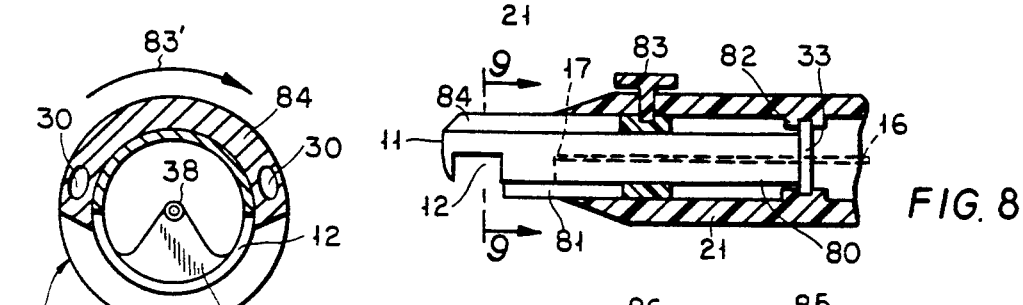
FIG. 8 is a diagram similar to FIG. 6, to show a second modification.
Figure 9:
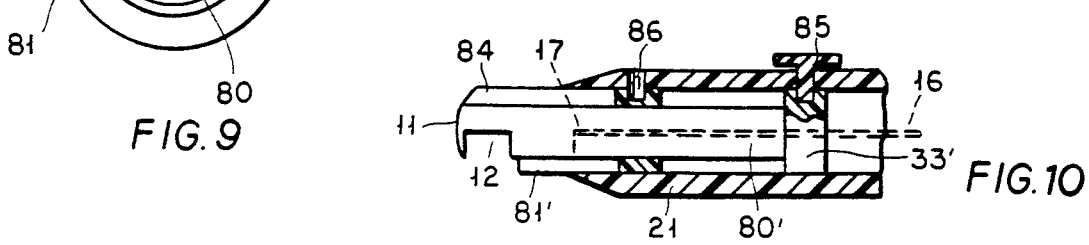
FIG. 9 is an enlarged sectional view, taken at 9—9 in FIG. 8.

In the arrangement of FIGS. 8 and 9, both of the inner and outer cannulas 80, 81 are longitudinally fixed with respect to handle 21. The inner cannula structure 80 has the same distal-end wall 11 and adjacent side port 12, as well as the posterior flange 33, via which it is additionally retained, as by keying means 82, against rotation with respect to handle 21. On the other hand, an externally exposed actuating button 83 has a radially inward stem formation locally engaged to the posterior end of the outer cannula structure 81, and a local arcuate slot in handle 21 will be understood to enable limited rotational displacement of the outer cannula structure 81. As seen in FIG. 9, the outer cannula structure 81 features an arcuate formation 84 of limited angular extent, such that at one limit of angular displacement the side port 12 is closed by formation 84, while at the other limit of angular displacement, the formation 84 clears side port 12, thus fully opening the same. Such angular displacement is suggested by arrow 83' in FIG. 9.

Figure 10:
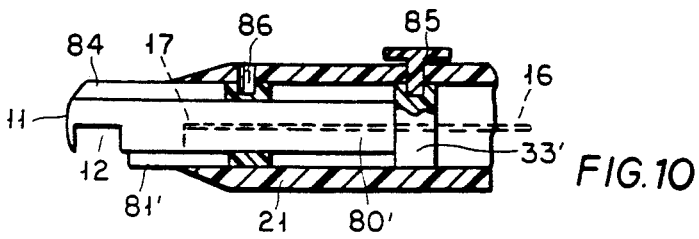
FIG. 10 is a diagram similar to FIG. 6, to show a third modification.

In the arrangement of FIG. 10, rotary actuation via button 85 effects rotation of the inner cannula 80' with respect to handle 21, while the outer cannula structure 81' is fixed as by a radial pin 86 to handle 21. Thus, the port-closure formation 84 of the outer cannula 81' may appear as in FIG. 9, but this is fixed to handle 21, while limited angular displacement of the inner cannula and its side port 21 is operative to determine the selectively open or closed condition of the distal end of the instrument. It will be understood that the stem portion of button 85 is accommodated in an arcuate slot, of limited angular extent, through the adjacent body thickness of handle 21.

In all embodiments of the invention, the leading edge of the distal end of the outer cannula will be understood to be preferably sharpened, as described above for the leading circular edge of the distal fitment 26, at adjacency with the cylindrical outer surface of the inner cannula. In the case of FIGS. 1 to 4, 6, and 7, the sharpened edge is on the distal fitment (26) at the distal end of the outer cannula. In the case of FIGS. 7 to 10, wherein relative rotation accomplishes opening and or closure of side port 12, it is the angularly spaced longitudinal edges of the formation 84 that are preferably sharpened, for equivalent tissue-cutting and port-closing purposes.

The described embodiments of the invention will be seen to achieve all stated objects of the invention. Cataractous lens material, be it nuclear or cortical, can be chopped away and fully engulfed within the cavity of chamber 40, and any connection between the engulfed material and material outside chamber 40 is guillotined by the sharp leading edge of the closure element, namely, the distal-end concaved contour of the outer cannula in the respective embodiments of FIGS. 1 to 4, 6, and 7, and the angularly limiting longitudinal edges of the arcuate closure formation 84, in the respective embodiments of FIGS. 8 and 9, and 10. Thus, a cutting or nibbling action can be observed in the course of cataract removal, without the potentially damaging consequences of ultrasonic phacoemulsification or other present-day practices. Furthermore, in contrast to experimental instruments presently known to use laser energy to remove cataractous tissue, the laser energy is applied within the fully closed chamber 40; thus, with the present invention, laser radiation affects no other tissue than the cataractous tissue contained within the closed chamber 40. Moreover, no laser energy is allowed to escape from the instrument to any portion of the eye, so that use of laser energy presents no damage potential to any part of the eye.

It should be clear that the present invention is not limited to use of any particular laser. For example, any polychromatic or monochromatic laser radiation can be used if the radiated energy is sufficiently high and of short enough duration to produce a hydrodynamic and acoustic shock wave that will micro-fragment or emulsify the cataractous tissue within the closed chamber 40.

What is claimed is:

1. A phaco-extractor tool for fragmenting and removing cataractous-lens tissue from the situs of fragmentation, said tool comprising elongate rigid tubular means having a central axis and having a distal working end and a proximal manipulation end, a rigid wall closure of said distal end and an arcuate side port locally adjacent said closure wall, said side port having a longitudinal dimension approximating the internal diametral extent of said tubular means and an arcuate extent in the range between 60° and 180° about said central axis; an elongate annular cannula slidably guided on and by said rigid tubular means, said cannula having a proximal infusion-port connection and distal-end porting for distal discharge of infusion liquid; selectively operable actuating means at said manipulation end for imparting relative reciprocation of said cannula and of said tubular means with respect to each other such that at one limit of relative displacement said cannula closes said side port and at an opposite limit of relative displacement said cannula no longer closes said side port; phaco-emulsification means including an active element contained within said tubular means and selectively operable upon tissue that has been scooped via the side port and into the distal end of said tubular means prior to cannula closure of the side port; said tubular means having an elongate internal passage communicating with said distal end and having an aspiration-port connection at said manipulation end; and said tool including an interlock element responsive to closure of the side port, said interlock element being operatively connected to effectively disable said phacoemulsification means unless said side port is in closed condition.

2. The phaco-extractor tool of claim 1 in which a manipulating handle is fixed to said rigid tubular means, whereby said cannula is longitudinally reciprocated to open and/or close said side port.

3. The phaco-extractor tool of claim 1, in which a manipulating handle is fixed to said cannula, whereby said tubular means is longitudinally reciprocated to open and/or close said side port.

4. The phaco-extractor tool of claim 1, wherein the distal end of said annular cannula has a sharpened circular cutting edge at its inner diameter of guidance by said rigid tubular means.

5. A phaco-extractor tool for fragmenting and extracting cataractous-lens tissue from the situs of fragmentation, said tool comprising elongate rigid tubular means having a central axis and having a distal working end and a proximal manipulation end, a rigid wall closure of said distal end and an arcuate side port locally adjacent said closure wall, selectively operable means carried by said tubular means for opening and for closing said side port, whereby when the side port is closed an enclosed chamber is defined within the distal end of said tubular means, phacoemulsifying means including a laser with optical-fiber delivery within said tubular means to a central point of laser irradiation into said chamber and at longitudinal offset from said end wall, infusion means forming part of said tool for discharging infusion liquid near but external to the distal end of said tubular means, and aspiration means including a through passage within said tubular means for externally extracting a flow of aspirated liquid and fragmented lens-tissue material from said chamber; said laser being remote from said tool and said laser including a flexible-cable connection for optical-fiber delivery of laser energy; and control means for said laser including an interlock with said selectively operable means so connected that said laser cannot discharge laser energy into said flexible-cable connection unless said interlock certifies that said side port is in closed condition.

6. The phaco-extractor tool of claim 5, in which said rigid tubular means includes a rigid guide tube on the central axis of said tubular means, said flexible cable being insertable in and removably guided by said guide tube, and clamping means at the proximal end of said tool for frictionally engaging and locating said cable such that its distal end of laser irradiation into said chamber is retained at said longitudinal offset from said end wall.

7. The phaco-extractor tool of claim 6, in which said clamping means is a bushing of elastomeric material mounted at the proximal end of said tool.

8. The phaco-extractor tool of claim 6, in which said guide tube is of stainless steel.

9. The phaco-extractor tool of claim 5, in which the proximal end of said tool has separate infusion and aspiration ports for flexible connection to an external source of infusion liquid and for flexible connection to an external aspiration system.

10. The phaco-extractor tool of claim 5, in which said flexible cable connection is a steel-sheathed optical fiber.

11. The phaco-extractor tool of claim 5, in which the optical-fiber delivery is via a detachable flexible-cable connection to said laser.

12. The phaco-extractor tool of claim 5, in which said selectively operable means includes actuating means carried at the proximal end of the tool, and a separate side port-closing element at the distal end of the tool, said actuating means and said side port-closing element being detachably connected.

13. The phaco-extractor tool of claim 5, in which said distal-end closure wall has a cutting edge adjacent the side port.

14. The phaco-extractor tool of claim 5, in which said means for opening and closing the side port has a cutting edge at a region of lap with the side port in the course of displacement to close the side port.

15. The phaco-extractor tool of claim 5, in which said control means includes selectively operable means for predetermining the total energy of laser irradiation for a given controlled irradiation discharge into said chamber.

16. The phaco-extractor tool of claim 15, in which said laser is a pulsed laser.

17. The phaco-extractor tool of claim 16, in which said total energy of a given controlled irradiation discharge is in the range of 0.05 to 3.0 Joules.

18. The phaco-extractor tool of claim 16, in which said total energy of a given controlled irradiation discharge is at least 0.05 Joules.

19. The phaco-extractor tool of claim 16, in which said total energy of a given controlled irradiation discharge is at least no greater than substantially 3.0 Joules.

20. The phaco-extractor tool of claim 5, in which the total energy of a given controlled irradiating discharge is in the form of a burst of 3 to 50 pulses wherein each pulse is of 50 to 300 microseconds duration.

21. The phaco-extractor tool of claim 5, in which the total energy of a given controlled irradiating discharge is in the form of a burst of 3 to 25 pulses per second for a period which is at least no greater than 2 seconds.

22. A phaco-extractor tool for fragmenting and removing cataractous-lens tissue from the situs of fragmentation, said tool comprising elongate rigid tubular means having a central axis and having a distal working end and a proximal manipulation end, a rigid wall closure of said distal end and an arcuate side port locally adjacent said closure wall, said side port having a longitudinal dimension approximating the internal diametral extent of said tubular means and an arcuate extent in the range between 60° and 180° about said central axis; an elongate annular cannula rotatable on said rigid tubular means and having a proximal infusion-port connection and distal-end porting for distal discharge of infusion liquid, the distal end of said cannular having an arcuate closure-flap which in one angular position closes said side port and in another angular position no longer closes said side port; selectively operable actuating means at said manipulation end for imparting relative rotation of said cannula end of said tubular means with respect to each other to establish one or the other of said angular positions; phaco-emulsification means including an active element contained within said tubular means and selectively operable upon tissue that has been scooped via the side port and into the distal end of said tubular means prior to cannula closure of the side port; said tubular means having an elongate internal passage communicating with said distal end and having an aspiration-port connection at said manipulation end, and said tool including an interlock element responsive to closure of the side port, said interlock element being operatively connected to effectively disable said phaco-emulsification means unless said side port is in closed condition.

23. The phaco-extractor tool of claim 22, in which a manipulating handle is fixed to said rigid tubular means, whereby said cannula is rotationally displaced to open and/or close said side port.

24. The phaco-extractor tool of claim 22, in which a manipulating handle is fixed to said cannula, whereby said tubular means is rotationally displaced to open and/or close said side port.

25. The phaco-extractor tool of claim 1 or claim 22, in which said phaco-emulsification means is a laser system with fiber-optic delivery of laser radiation within said tubular means to a location of discharge short of the distal end.

26. The phaco-extractor tool of claim 1 or claim 22, in which said phaco-emulsification means is a laser system with fiber-optic delivery of laser radiation within said tubular means to a location of discharge short of the distal end, said tubular means including a fixed tubular guide for an optical fiber forming the delivery portion of said laser system.

27. The phaco-extractor tool of claim 1 or claim 22, wherein said rigid end-wall closure has a locally sharpened cutting edge adjacent said side port.

28. The phaco-extractor tool of claim 22, wherein said closure flap has a sharpened longitudinal cutting edge at least at one of the angular limits of said closure flap.

* * * * *